United States Patent [19]
Yoshimi et al.

[11] Patent Number: 4,928,090
[45] Date of Patent: May 22, 1990

[54] AROUSAL LEVEL JUDGING APPARATUS AND METHOD

[75] Inventors: Tomohisa Yoshimi, Gamagori; Satoru Kodama, Oobu; Takeshi Yoshinori, Chiryu; Masahiko Ito, Nagoya, all of Japan

[73] Assignee: Nippondenso Co., Ltd., Kariya, Japan

[21] Appl. No.: 281,074

[22] Filed: Dec. 8, 1988

[30] Foreign Application Priority Data

Dec. 9, 1987 [JP] Japan ................................. 62-312972
Jul. 18, 1988 [JP] Japan ................................. 63-178793

[51] Int. Cl.$^5$ ............................................. G08B 21/00
[52] U.S. Cl. ................................. 340/575; 128/734; 340/576
[58] Field of Search ................. 340/576, 575; 128/734

[56] References Cited

U.S. PATENT DOCUMENTS

4,088,125 5/1978 Forgione et al. .................. 128/734
4,725,824 2/1988 Yoshioka ............................ 340/576

OTHER PUBLICATIONS

"Feedback Control of the Level of Arousal Using Skin Potential Level as an Index", by Chiaki Nishimura et al.; Ergonomics 1985, vol. 28, No. 6, pp. 905–913.
"Estimation of the Level of Arousal by Skin Potential and its Application to Sleep Control", by Chiaki Nishimura et al.; MBE 83-27; pp. 53–60.
"Evaulation of the Arousal Level in Motorcar Driving Using Skin Potential Level I: Changes in Skin Potential Level Under Various Driving Conditions", by Chiaki Nishimura et al.; from Ningen Kogaku, vol. 23, No. 2('87), pp. 103–110.
"Evaluation of the Arousal Level in Motor Driving Using Skin Potential Level II: Its Effectiveness Compared with Other Electrophysiological Quantities", by Chiaki Nishimura et al.; from Ningen Kogaku, vol. 23, No. 2('87); pp. 111–118.
"Biofeedback of Skin Potential Level for Sleep Control", by Chiaki Nishimura et al.; from Kenkyu, vol. 18, No. 5 (Sep. 1980); pp. 327–333.
"Feedback Control of the Level of Arousal in Motor Driving", by Chiaki Nishimura et al.; from Biofeedback Kenkyu (1984).

*Primary Examiner*—Glen R. Swann, III
*Attorney, Agent, or Firm*—Cushman, Darby & Cushman

[57] ABSTRACT

An arousal level judging apparatus has a skin potential level (SPL) detection device, a potential change detection device for detecting occurrance and convergence of a pulse of the signal from the SPL detection device, the pulse being caused by skin potential response (SPR), a storing device for storing the SPL value as a reference value, and a comparator for comparing SPL with the reference value to detect a SPL decrease to detect an arousal level decrease of a driver, etc. The reference value is renewed at every occurrance of SPR. When the SPL value indicates that the arousal level of the driver has been decreased, an alarm is caused to wake the driver up.

12 Claims, 11 Drawing Sheets

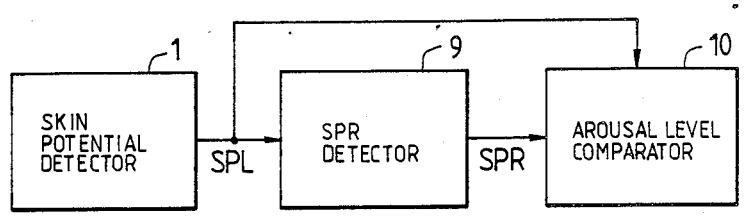
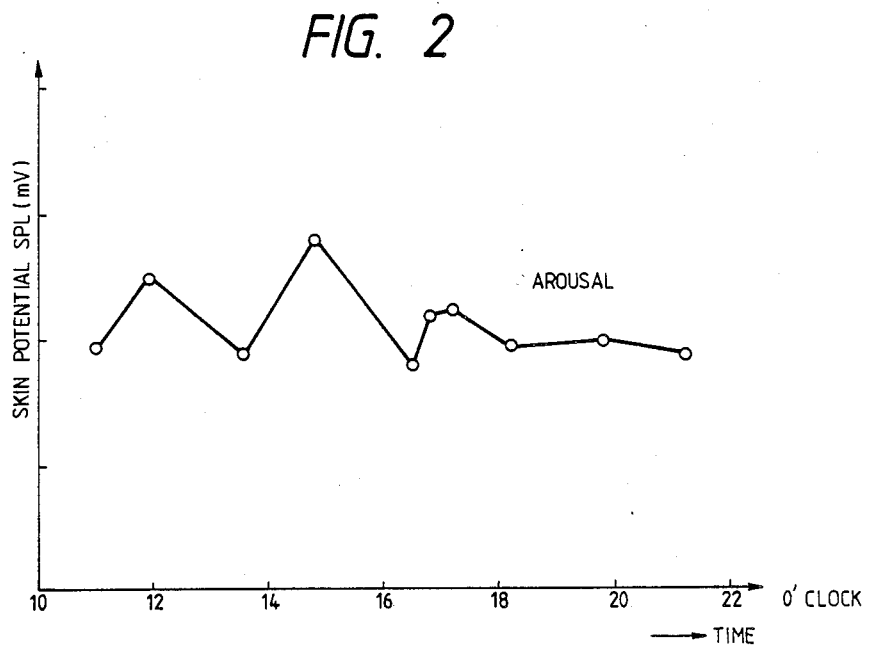

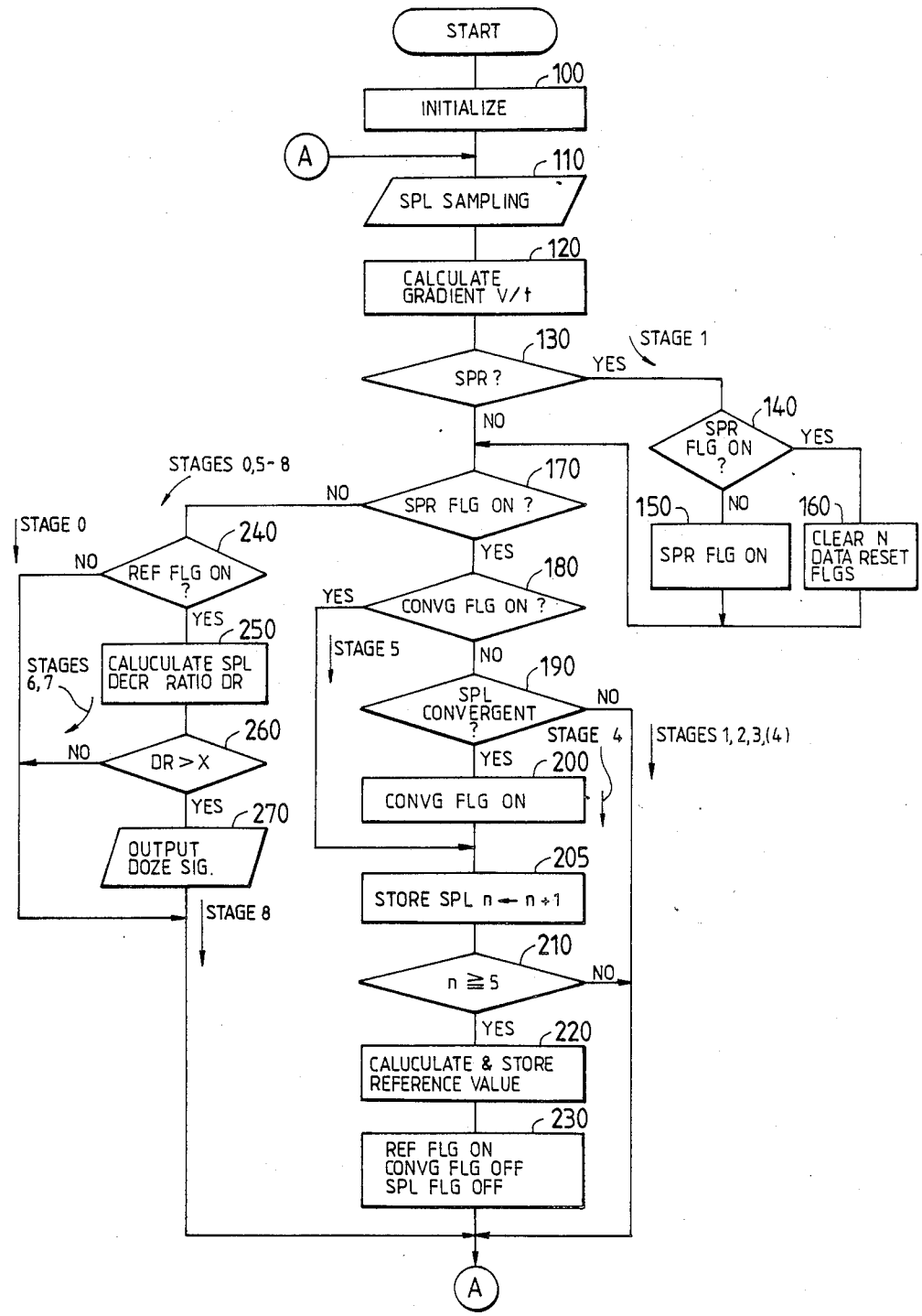

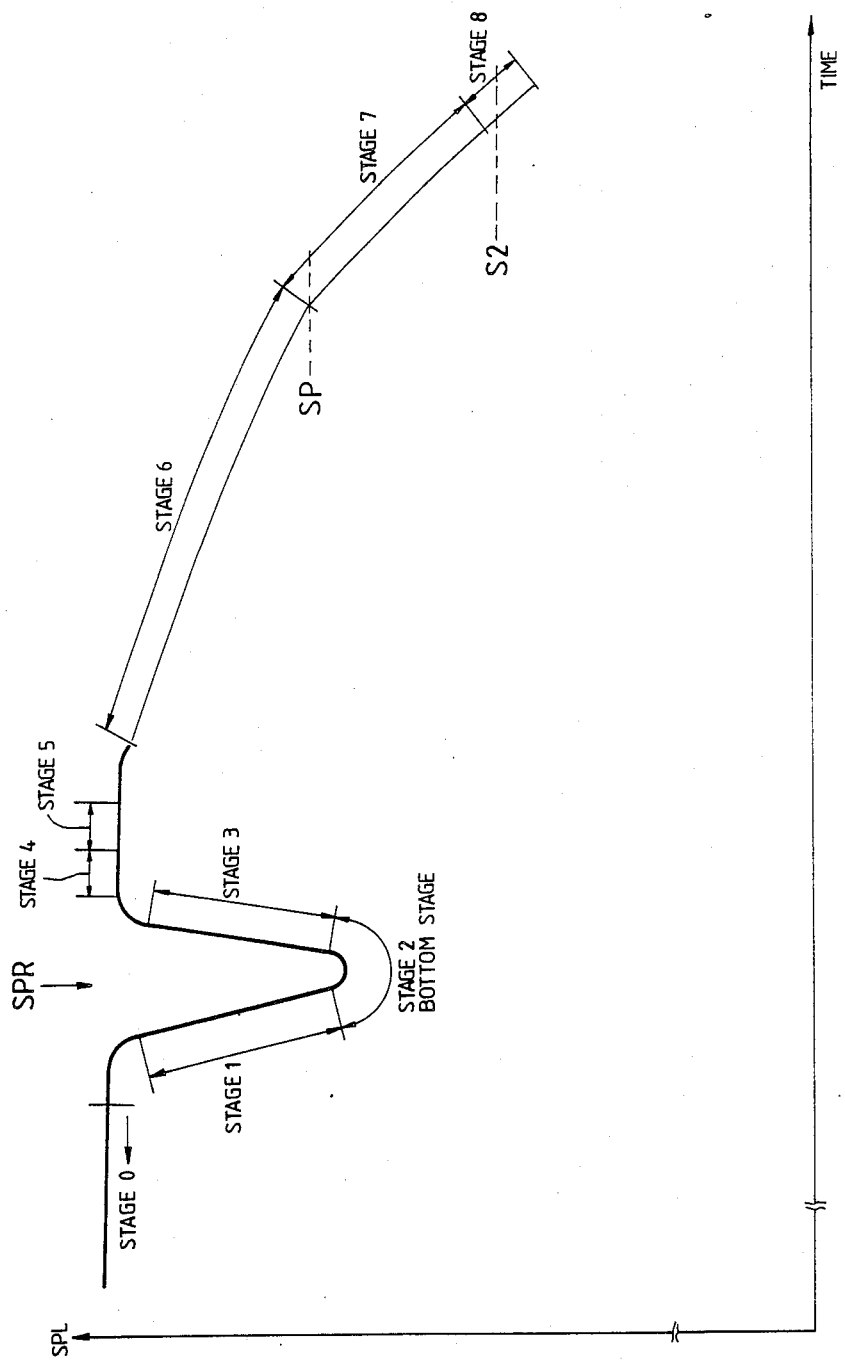

AROUSAL LEVEL JUDGING APPARATUS AND METHOD

BACKGROUND OF THE INVENTION

1. Field of the Invention

This invention relates generally to an arousal level judging apparatus used for detecting an arousal level of an operator or a patient and more particularly, the invention relates to apparatus for detecting drowsiness during driving an automobile, which is applicable to a doze alarm system.

2. Description of the Prior Art

The main types of arousal level judging apparatus used for detecting the driver falling asleep which are known comprise; detection means having electrodes attached to a human body for detecting a skin potential level (hereinafter referred to as SPL) and a comparator for comparing the signal from the detection means with the predetermined value. Such technique has been described in Japanese patent application provisional publication No. 60-139539.

Generally, electrophysiological signals are known to have individual differences and variations within a day, i.e., diurnal variation. SPL also varies with diurnal variation, as shown in FIG. 2.

In the above-mentioned Prior art, in order to obtain a reference value to determine decrease ratio of SPL for judging a person falling asleep, a pre-experiment of sleep should be made before such detection of falling asleep is made actually because the reference value is required for compensation for the individual difference and diurnal variation.

However, an arousal level judging apparatus using the above-mentioned technique lacks ease in operation because such apparatus requires a user, for example, a car driver, to be subjected a pre-experiment of sleep. Although a compensation for general individual differences can be obtained through the above-mentioned pre-experiment, this compensation is ineffective for diurnal SPL variation because the reference to SPL will change with the passage of time.

Therefore, in the Prior art arousal level judging apparatus, there are drawbacks that it is difficult to obtain the reference to SPL, and that the reference should be determined at every predetermined intervals.

SUMMARY OF THE INVENTION

The present invention has been developed in order to remove the above-described drawbacks inherent to the conventional arousal level judging apparatus.

It is, therefore, an object of the present invention to provide a new and useful arousal level judging apparatus which is capable of detecting arousal level decrease without such pre-experiment and to renew the reference with the passage of time.

According to a feature of the present invention, the reference of SPL is obtained just after a pulse-like change of SPL, i.e., skin level potential response (hereinafter referred to as SPR), is substantially converged. The convergence of SPR is detected by SPR convergence detection means. The reference is stored by SPL storing means responsive to SPR convergence detection means. SPR occurs in accordance with an environmental change received by the user, i.e., subject. The occurrence of SPR reflects high arousal level of the user. This indicates that SPL of SPR-occurrence state can be adopted as a reference for detecting decrease in arousal level. This is done by storing the value of SPL. Then, SPL is compared with the reference value by a comparator for detecting a decrease in arousal level. SPL is detected by SPL detection means.

In accordance with the present invention there is provided an arousal level judging apparatus having SPL detection means, SPR convergence detection means, storing means for storing a reference value, SPL decrease ratio detection means which detects decrease of SPL by comparing measured SPL with a value obtained by multiplying the reference value with a predetermined value, and a comparator for further comparing decrease ratio with another predetermined value for detecting higher degree of SPL decrease than that detected by the SPL decrease ratio detection means, responsive to SPL decrease ratio detection means.

In accordance with the present invention there is further provided an arousal level judging apparatus comprising: skin potential level detection means for detecting skin potential level of a human body; level change detection means (110, 120) for detecting the degree of change in the level of an output signal of said skin potential level detection means over a predetermined interval; a comparing means (130) for comparing said degree from said level change detection means with a first predetermined value to detect the presence of a pulse-like change in said skin potential level; convergence detection means (190) responsive to an output signal from said comparing means (130) for detecting a non-pulse like portion in said skin potential level by analyzing succesive change of gradient determined by said degree from said level change detection means; storing means (220) for storing said skin potential level as a reference value when non-pulse like portion is detected by said convergence detection means; and arousal level detecting means (250, 260) responsive to said skin potential level from said skin potential level detection means and to said reference value from said storing means for determining arousal state and non-arousal state of said human body using the relation ship between said skin potential level and said reference value.

In accordance with the present invention there is further provided an arousal level judging apparatus comprising: skin potential level detection means for detecting skin potential level of a human body; level change detection means (410, 420) for detecting the degree of change in the level of an output signal of said skin potential level detection means over a predetermined interval; a comparing means (430) for comparing said degree from said level change detection means with a first predetermined value to detect the presence of a pulse-like change in said skin potential level; convergence detection means (440) responsive to an output signal from said comparing means (430) for detecting a non-pulse like portion in said skin potential level by analyzing successive change of gradient determined by said degree from said level change detection means; storing means (480) for storing said skin potential level as a reference value when non-pulse like portion is detected by said convergence detection means; and a calculation means (490) for obtaining a set point value by multiplying said reference value by a constant smaller than one; arousal level detection means (500) for determining non-arousal state of said human body when said skin potentiol level in below said set point value and the gradient of the change of said skin potentia 1 level below said set point value is grater than a second predetermined value.

The present invention also defines a method for accomplishing the above discussed objectives.

BRIEF DESCRIPTION OF THE DRAWINGS

The object and features of the present invention will become more readily apparent from the following detailed description of the preferred embodiments taken in conjunction with the accompanying drawings in which:

FIG. 1 is a general block diagram of the present invention;

FIG. 2 is a drawing showing a SPL variation within a day;

FIGS. 8A and 8B are flow charts of the first embodiment;

FIG. 8D is a drawing showing an SPL variation curve divided in nine stages;

The same or corresponding elements and parts are designated at like reference numerals throughout the drawings.

DETAILED DESCRIPTION OF THE INVENTION

Figure 3:
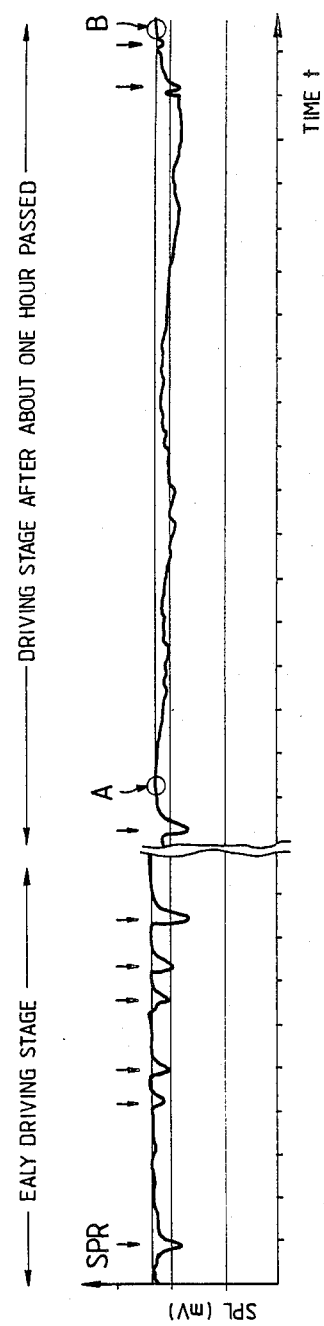
FIG. 3 is a drawing showing a typical SPL variation curve during driving an automobile.

Referring to FIGS. 1 to 6, 8A, 8B and 8D, a first embodiment of the present invention will be described.

FIG. 1 is a functional block diagram showing basic functions performed by the arousal level judging apparatus according to the present invention which are common to all the embodiments. In FIG. 1, an arousal level judging apparatus comprises a skin potential detector 1 which detects skin potential level (SPL) of human body, a SPR detector 9 for detecting pulse type of SPL variation, i.e., for detecting skin potential response (SPR) occurrence and convergence of SPR, responsive to the skin potential detector 1, and for storing SPL value, and an arousal level comparator 10 for comparing stored SPL with current SPL to detect arousal level decrease. Here, convergence of the SPL curve means that SPL change due to SPR reaches non-pulse like portion, i.e., stage 4 shown in FIG. 8D, through stages 1 to 3.

The arousal level judging apparatus of the first embodiment mounted in an automobile detects a decrease of arousal level of an automobile driver and alarms the driver by an alarm bell and wakes the driver up.

Hereinbelow will be described a general operation of the arousal level judging apparatus.

FIG. 3 shows variation of SPL during driving an automobile. In early stage of driving a car, SPL stays at a high level and several SPRs occur with environmental changes, i.e., stimuli such as conversation and passing another car ahead.

However, SPL begins to decrease gradually after about one hour has passed because of acclimatization to driving of the car and driving environment. In this stage, the frequency of SPR occurrences decrease, then, SPL decreases with sawtooth variations. This state continues until a large amount of stimuli, such as conversation, is applied to the driver. In other words, occurrence of SPR indicates the driver at a high arousal level.

The first embodiment has made for judging decrease in arousal level, utilizing the reference obtained from convergence of SPL curve due to SPR and decrease ratio of SPL to the reference.

Hereinbelow will be described detection of SPR where SPL change of SPR should be distinguished from SPL diurnal change and decrease of the arousal level.

Figure 4:
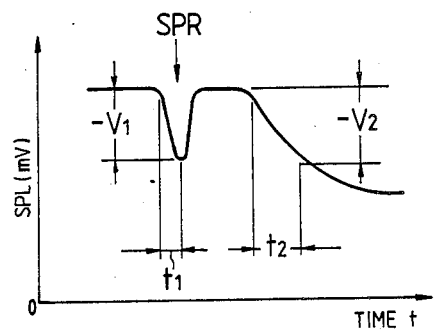
FIG. 4 is a drawing showing a SPL variation curve with SPR and another SPL variation.
Figure 5:
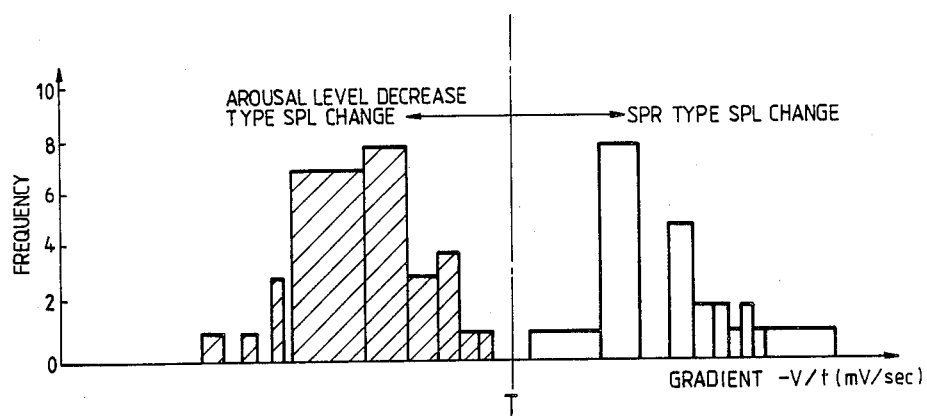
FIG. 5 is a histogram of SPL gradients.

FIG. 4 shows a SPL variation curve with SPR and another SPL variations. This SPL variation curve is experimentally obtained and is schematically illustrated. FIG. 5 is a histogram showing frequencies of sampled data of SPL with respect to gradient of SPL curves. The occurrence frequency of arousal level decrease type is indicated by hatched bars. The scale of the transverse is logarithm.

FIG. 4 shows that SPL gradient of SPR ($-V_1/t_1$) is larger than that of diurnal change or decrease in arousal level ($-V_2/t_2$). FIG. 5 shows the difference in occurrence inclination between SPL decrease of SPR and that of other causes with respect to V/t. Therefore, occurrence of SPR can be detected by comparing $-V/t$ of SPL variation with a threshold level T. The absolute value of SPR gradient is larger than that of other causes.

Figure 6:
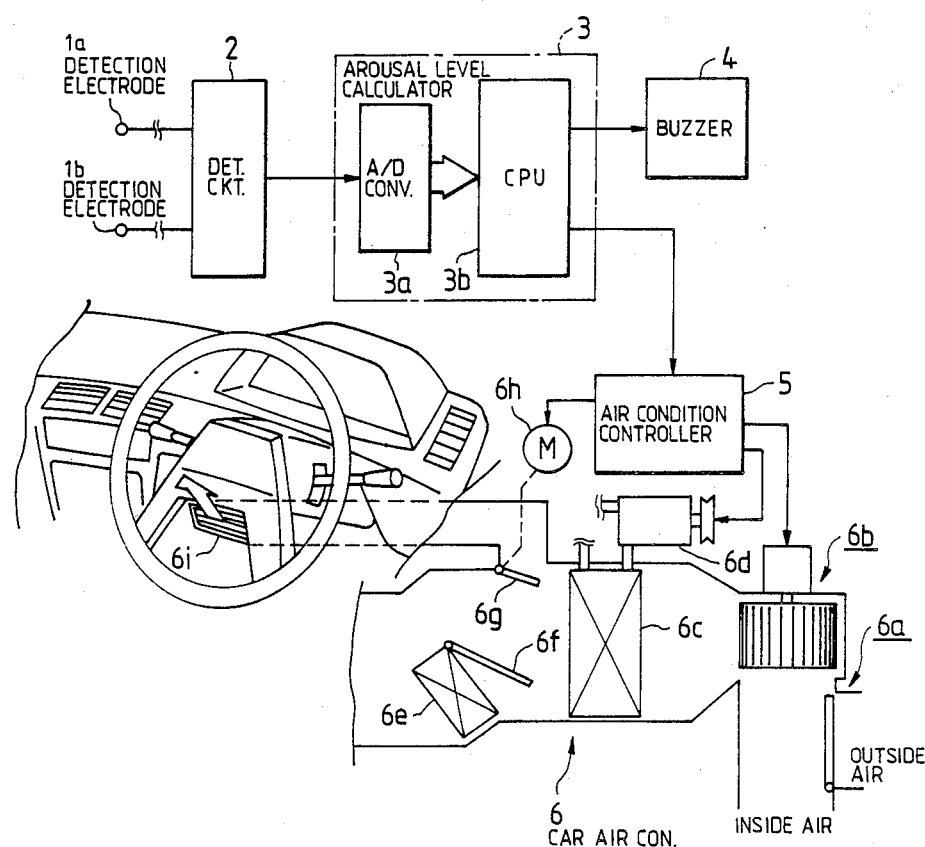
FIG. 6 is a block diagram of a first embodiment.

FIG. 6 shows a block diagram of an arousal level judging apparatus according to the present invention.

In FIG. 6, SPL detection electrodes 1a, 1b are attached to the forearm of a driver and to the thenar area of the palm with paste, etc. The electrodes 1a, 1b are skin electrodes made of Ag-AgCl, etc. A detection circuit 2 differentially amplifies SPL signals from the electrodes 1a, 1b of the forearm and palm up to a several-volts level and outputs positive SPL signal (hereinafter referred to as SPL signal). The arousal level calculator 3 has A/D converter 3a which converts an analog SPL signal into a digital signal and a micro-computer (hereinafter referred to as CPU) 3b which executes the program mentioned later. A buzzer 4 and air condition controller 5 operate in response to signals from the CPU 3b. A car air conditioner 6 comprises a control damper 6a for selecting fresh or recirculated air, blower 6b, evaporator 6c, compressor 6d, heater 6e, air mixing damper 6f, by-pass damper 6g, by-pass servo motor 6h, by-pass air vent 6i, etc. The air vent 6i is directed toward the face of the driver.

Hereinbelow will be described structure of the first embodiment of the arousal level judging apparatus with respect to FIG. 6.

In FIG. 6, the operation of ignition key (unshown) causes the arousal level judging apparatus to be supplied with power and this causes CPU 3b to start executing a program of arousal level judgement. When CPU 3b judges the driver's arousal level to be low, CPU 3b sends a drowsiness signal to the buzzer 4 and the air condition controller 5. The buzzer 4 alarms in response to the drowsiness signal and gives a driver a warning in order to prevent the driver from sleeping. The air condition controller 5 also operates the blower 6b, the compressor 6d, by-pass servo motor 6h which opens the by-pass damper 6g, in response to the drowsiness signal, thereby, blowing a cool air toward the driver's face. This causes the driver to be aroused.

Hereinbelow will be described general operation of the first embodiment.

In FIG. 3, SPLs just after SPR occurrences respectively returns to nearly the same level. When SPR occurs in a drive stage of about one hour passed, the decreased SPL returns to the level B which is nearly the same as level A from which SPL begins to decrease. Therefore, an SPL just after occurrence of a SPR shows SPL of the driver at a high arousal level. The arousal level judging apparatus of the first embodiment stores the value of SPL just after a SPR occurrence as a reference value for determining SPL decrease ratio, as well as the reference is renewed at every occurrence of SPR. This makes it possible to judge the arousal level decreased to drowsiness level, eliminating effects of diurnal variation, acclimatization, and individual differences. In the first embodiment of the arousal judging apparatus, a decrease ratio of SPL is obtained by the following equation:

$$\text{decrease ratio of } SPL = \text{present } SPL/SPL \text{ just after } SPR \text{ occurrence} \quad (1)$$

In an experiment, such as shown in FIG. 3 made by the inventors, subjects of car drivers said that they had felt drowsiness when the decrease ratio of SPL decreased to a range from 0.6 to 0.8. Therefore, the arousal level judging apparatus is so designed as to judge a driver drowsiness when the decrease ratio of SPL decrease to this range.

The above-mentioned operation can be performed by a CPU 3b. Hereinbelow will be described operation of the CPU 3b of the first embodiment with reference to FIG. 8A of a flow chart.

The CPU 3b starts an operation with turning power on, then, entering the operation flow shown in FIG. 8A at step 100. In step 100, an initialization is made for clearing a RAM and setting flags, etc. Next, in step 110, the CPU 3b reads a value of SPL from A/D converter 3a and stores the value of SPL k (k indicates the number of times processing at step 110). In the succeeding step 120, the CPU 3b calculates gradient of SPL change $-V/t$ (t is unit time interval) for detection of SPR occurrence. In actually, the CPU 3b subtracts the value of SPL k−1 from that of SPL k and waits for time interval t. This shows gradient of SPL change. Practically, processing time interval should be considered. However, because process speed is extremely high and processing time interval is not so long comparing with time interval t, thus, process time interval can be omitted. A decision is then made, in step 130, as to whether the resultant gradient is lower than a predetermined value T, i.e., threshold level T, for detecting a pulse of SPR, i.e., detecting the gradient of SPL, as indicated by $-V1$ and t1 in FIG. 4 which is lower or steeper than the gradient $-V2/t2$. If the resultant gradient is lower than the predetermined value T then this indicates that the present change of SPL is made by SPR, in which case step 140 is executed. At the first processing of step 130, the CPU 3b decides SPL change of SPR does not occur, then processing proceeds around the loop of steps 170, 240, 270, and 110, until the SPL change of SPR is detected in step 130, i.e., SPL change enters stage 1 shown in FIG. 8D. If SPR is detected in step 130, process proceeds through step 150, in which SPR flag is set, to step 170 in which detects SPR flag. If SPR flag is detected, then process proceeds through step 180 to step 190. A decision is made in step 190 as to whether convergence of SPR pulse is detected. If convergence of SPR pulse is detected, i.e., this means SPL change enters stage 4 shown in FIG. 8D, SPR convergence flag is set in step 200. Then, the value of SPL n is stored and process proceed to step 110 through step 210. At the first operation of step 190, the CPU 3b decides that SPR has not converged, then processing returns to step 110.

Now, the SPR convergence flag is set at every detection of SPR and is reset at every processing of step 230. If the SPR convergence flag is set in step 200, i.e., this means SPL enters stage 4, 5, it forbids the CPU 3b to proceed to the loop of steps 240–270 until a reference value is finally determined in step 220.

The SPR convergence flag forbids the CPU 3b to read the value of SPL during stage 1, 2, and 3. When it is detected that gradients of SPL change, i.e., positive and negative values of V/t, are in the predetermined ranges, the SPR convergence flag is set in step 200. The flag permits the CPU 3b to read SPL in for determination of the reference value.

Figure 8B:
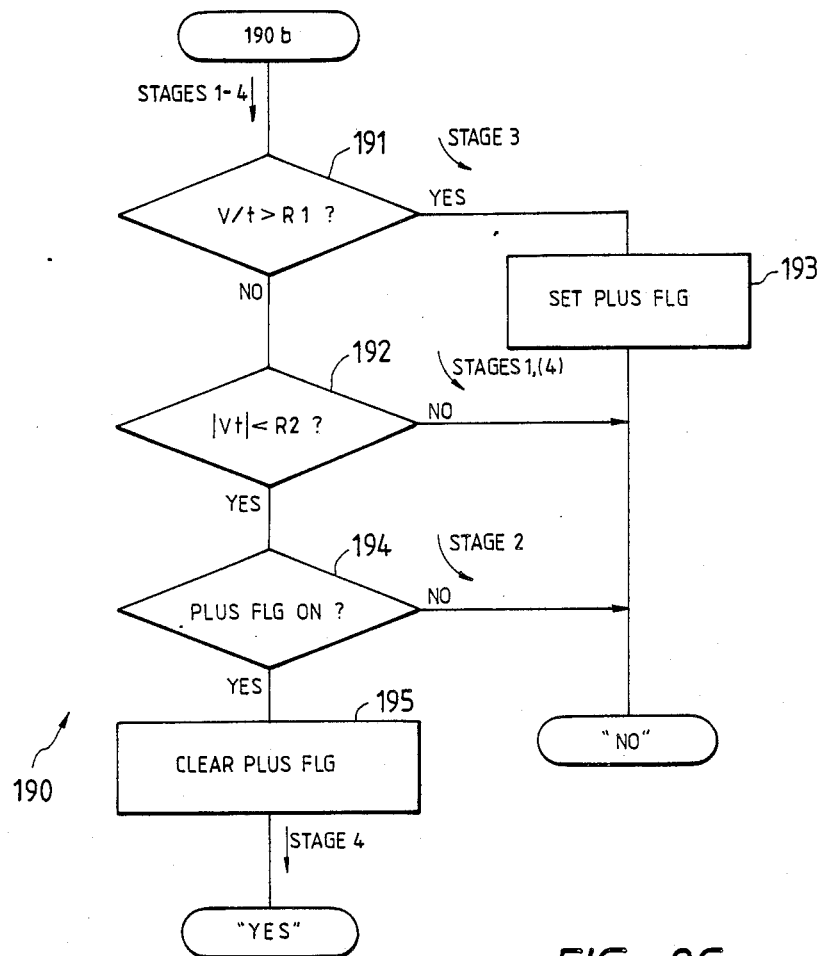

FIG. 8B shows the process of step 190 more clearly. The process of step 190 begins at step 190b. A decision is made in the successive step 191, as to whether the gradient of SPL change is greater than a positive predetermined value R1. If a gradient is larger than the positive predetermined value R1, i.e., this means SPL change enters stage 3, process proceeds to step 193. At the first operation of step 191, a gradient is smaller than the predetermined value R1, then this indicates that the SPL change enters stage 1 shown in FIG. 8D. Then, a decision is made in step 192, as to whether a gradient of SPL is nearly equal to zero, then this indicates that the present SPL reaches convergence of SPR pulse. At the first operation of step 192, the CPU 3b judges the gradient not equal nearly to zero, then process progresses to "NO" of step 190, i.e., to step 110. If SPL change enters stage 3 shown in FIG. 8D, the CPU 3b judges SPL gradient positive then setting a plus flag in step 193. In convergence stage of SPR, i.e., stage 4, process progresses through step 191, to step 192. The CPU 3b judges a gradient nearly equal to zero, then process progresses to step 194. A decision is made as to whether the plus flag has been set, then this indicates that SPL change has passed the bottom of SPL change of SPR. Therefore, if SPL change reaches the bottom stage of SPR the operation progresses to "NO" of step 190. In convergence stage of SPR, process progresses to step 195. Then, the CPU 3b detects convergence of SPL change of SPR. In the successive step 195, the CPU 3b resets the plus flag. Then, process progresses to "YES" of step 190.

Next, the process progresses to step 200 in FIG. 8A. The CPU 3b sets the convergence flag. In step 205, the CPU 3b stores a value of SPL, then the processes progresses around the loop of steps 205, 210, 110, 170, 180, 205, and 210 until the loop count reaches 5 in counting steps 205 and 210. However, if another SPR occurs during process of the loop of steps 205, 210, 110, 170, 180, 205, and 210, process branches off at step 130 and proceeds to steps 140 and 160, then, the stored SPL data and convergence, plus, and zero flags are cleared and the CPU 3b begins storing new SPL data.

When the counting has finished at step 210, the CPU 3b averages five stored SPL values and stores the resultant mean data as a reference value in step 220. In the succeeding step 230, a reference flag is set and convergence and SPR flags are reset, then process returns to step 110. Therefore, in this status, the CPU 3b is permitted to execute the calculation process of steps 240, 250, 260, and 270 in step 170. Then, processing proceeds to steps 250 and 260. If SPL decrease ratio is lower than a predetermined value X, then the doze signal is sent to the buzzer 4 and air-condition controller 5 in step 270. If not so, processing returns to step 110.

Then, the buzzer 4 alarms and the air-condition controller 5 operates the blower 6b, compressor 6d as well as opens the by-pass damper 6g in order to supply a cool air toward the driver in response to the drowsiness signal. Therefore, the driver is notified his arousal level has decreased and is aroused by the cool air.

As stated hereinabove, the arousal level judging apparatus of the first embodiment stores the value of SPL just after SPR occurrence as a reference value for determining SPL decrease ratio, as well as the reference is renewed at every occurrence of SPR. This makes it possible to judge arousal level of the driver having been decreased to drowsiness level, eliminating effects of diurnal variation, acclimatization, individual difference. Therefore, the arousal level judging apparatus of the first embodiment provides accurate detection of arousal levels.

Hereinbelow will be described the second embodiment.

Figure 7:
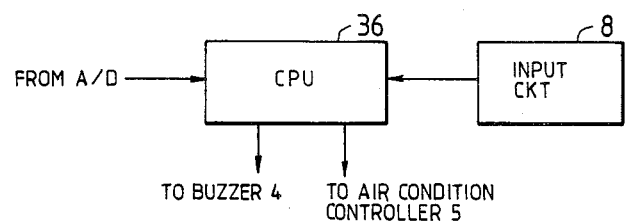
FIG. 7 is a partial block diagram of a second embodiment showing a portion of FIG. 6.

An arousal level judging apparatus of the second embodiment has a similar structure to the first embodiment However, the second embodiment operates according to the program of FIG. 8A. Also input circuit 8 shown in FIG. 7 is provided which receives and sends data to the CPU 3b. Therefore, a detailed description of the circuit arrangement of the second embodiment is omitted.

Figure 9A:
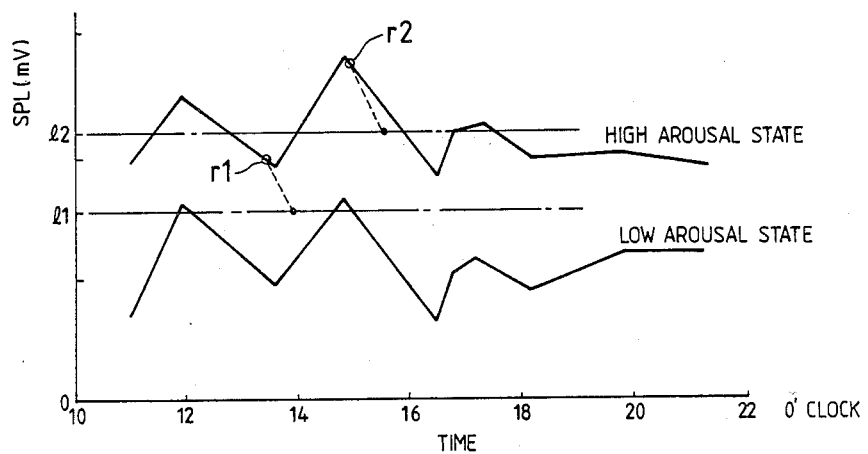
FIG. 9A is a drawing showing a SPL variation within a day.
Figure 9B:
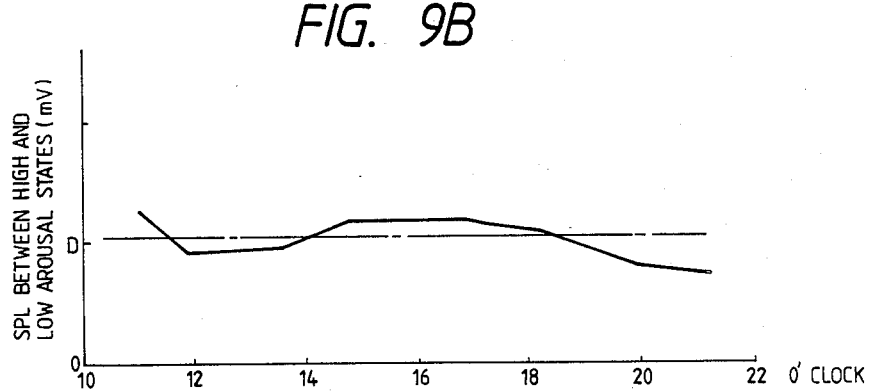
FIG. 9B is a drawing showing a difference variation of SPL between high and low arousal states.

FIG. 9A represents SPL diurnal variations of high arousal level and low arousal level. FIG. 9A is obtained through an experiment. The experiment was made as follows:

In an ordinary room, SPL of a subject is measured by using detection electrodes attached to his body. The subject is given high and low arousal states alternately at a predetermined interval, for example, five or twenty minites. The high arousal state is made by conversation. The low arousal state is made by leaving the subject at a rest-and-closing eye state. The experiment was done from about 10 o'clock to 22 o'clock. Next, obtained SPLs of high arousal and low arousal levels are plotted respectively, as shown in FIG. 9A. Here, low arousal state means a rest-and-closing eyes state but not sleeping state. This means that rest-and-closing eye states is dangerous when driving a car. FIG. 9B shows the difference between high arousal level and low arousal level.

In FIG. 9A, SPL which has been obtained from a human being in high arousal state varies as the passage of time within a day, as shown by an upper curve. As described above, in the first embodiment, the arousal level judging apparatus calculates SPL decrease ratio as defined by Eq. (1) by using absolute values of SPL. This means that when the reference value is high, decrease amount of SPL is large and when the reference value is low, decrease amount of SPL is small. In other words, in the method according to the first embodiment it is assumed that decrease amount of SPL representing the same arousal level decrease is proportional to the reference value. However, experiments show that SPL difference between high and low arousal levels, for each driver is substantially constant, as shown in FIG. 9B. Therefore, if degree of arousal level decrease are the same between high and low arusal states, SPL decrease amounts should also be changed in accordance with the varying reference value. Then, the predetermined value X should be changed in accordance with reference values. In the second embodiment, the decrease ratio is calculated on the basis of the diference D which is a mean value, as shown in FIG. 9B. Experiments also show that the difference D is different from one another between drivers. Therefore, in the second embodiment of the present invention, input means 8 is provided which receives and sends individual data to the CPU 3b. The CPU 3b calculate SPL decrease ratio by the following equation:

$$SPL \text{ decrease ratio} = (\text{reference value} - \text{present } SPL)/SPL \text{ difference between high and low arousal levels } (D) \quad (2)$$

Figure 8C:
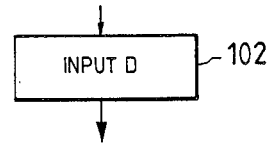
FIG. 8C is an additional flow chart of a second embodiment which is executed after step 100 of FIG. 8A.

In the second embodiment of the present invention, the CPU 3b is operated by the program shown in the flow diagram of FIG. 8A and SPL difference D is inputted to CPU 3b in step 102, as shown in FIG. 8C, which is located just after step 100 and the equation (2) is used in step 250 in FIG. 8A.

In this way, the arousal level judging apparatus of the second embodiment can judge the arousal level of a driver more accurate than the first embodiment because arousal level is determined on the basis of SPL difference D for normalization in the second embodiment, whereas, in the first embodiment, arousal level is determined on the basis of SPL difference between the reference value and zero level. In addition, difference D can be inputted individually, so that arousal level can be judged more accurate than the arousal level judging apparatus of the first embodiment. Moreover, difference D may also be preset in the CPU 3b. Further, arousal level decrease can also be detected in steps 250, and 260 by comparing SPL decrease which is obtained by substracting the present value of SPL from the reference value with a predetermined value.

Hereinbelow will be described the third embodiment of an arousal level judging apparatus of the present invention.

The third embodiment of the arousal level judging apparatus has the same structure as that of the first embodiment but uses the program of FIG. 13A-13B for CPU 3b as described later. Therefore, a detailed description of the circuit arrangement of the third embodiment is omitted.

Figure 11:
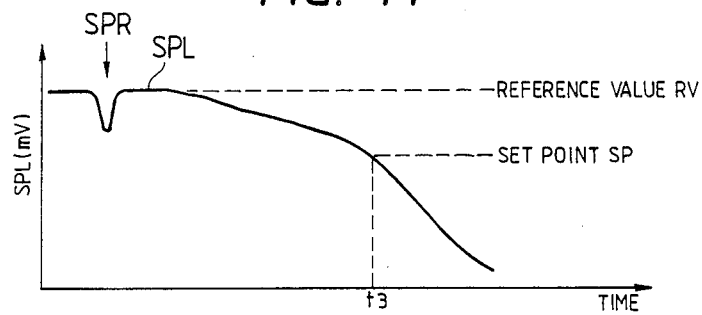
FIGS. 11 and 12 are drawings showing SPL variation curves.
Figure 12:
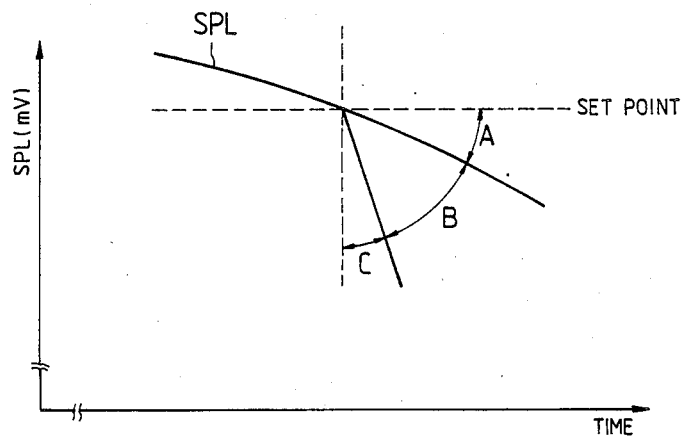

FIG. 11 shows a curve of SPL variation when a driver falls asleep. In the early stage of driving a car, a change of SPL due to SPR occurs. Then, SPL decreases from a reference value RV to a set point SP with the time passing because of acclimatization. The SPL variation curve below the set point SP has a larger gradient than that from the reference value to the set point. This SPL variation curve shows that the driver falls almost asleep after time t3. Therefore, a decrease of arousal level can be detected by the gradient of SPL curve below the set point. FIG. 12 shows three types of SPL decrease curves below the set point; gradient ranges A, B, and C. The decrease curve of SPL within gradient range A results from diurnal variation of SPL or acclimatization to driving circumstance. The decrease curve of SPL within the gradient range C is caused by an external stimulus. Therefore, decrease of SPL can be detected by a gradient within the gradient range B. The arousal level judging apparatus of the third embodiment detects decrease of arousal level by the gradient of SPL curve below the set point which is determined by the reference value. The reference value is obtained from SPL just after occurrence of SPR.

The operation of the CPU 3b of the third embodiment will now be described with reference to FIGS. 13A and 13B.

Figure 13A:
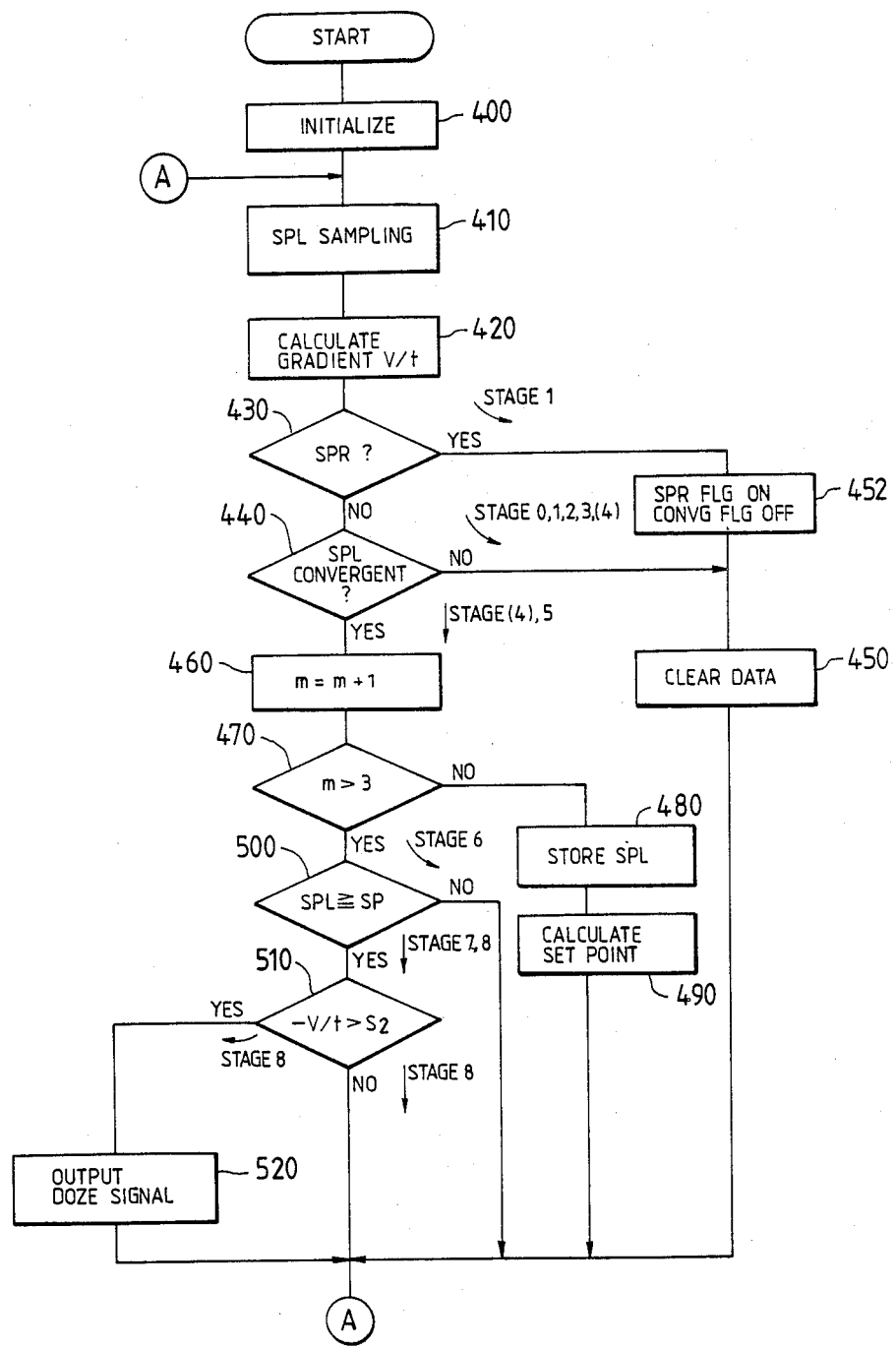
FIGS. 13A and 13B are flowcharts of a third embodiment.

The CPU 3b of the arousal level judging apparatus of the third embodiment operates, as shown in FIG. 13A, by first determining a set point from the reference value. Then, if SPL decreases to the set point and further SPL decreases at a greater ratio of decrease ratio than a predetermined ratio, i.e., the gradient of the SPL curve becomes steeper than before after the set point SP, the CPU 3b sends a doze signal to the buzzer 4 and air-conditioning controller 5 to arouse the driver.

More specifically, the CPU 3b starts an operation with power being supplied, then, entering the operation flow shown in FIG. 13A at step 400. In step 400, an initialization is made for clearing a RAM and setting flags as well as set initial data for controlling, such as a predetermined value S1 for judging SPR occurrence through SPL variation and a predetermined value S2 for judging SPL decrease due to an arousal level decrease. Next, in step 410, the CPU 3b reads a value of SPL from A/D converter 3a and stores the SPL k (k indicates the number of times of processing at step 410). In the succeeding step 420, the CPU 3b calculates gradient of SPL change $-V/t$ for detection of SPR. In actuality, the CPU 3b subtracts the value of SPL $k-1$ from that SPL k and waits for time interval where t (t is unit time). This shows gradient of SPL change. A decision is then made, in step 430, as to whether the resultant gradient is smaller than a predetermined value T for detection of SPR, i.e., detecting a pulse of SPR, i.e., detecting the gradient of SPL indicated by $-V1$ and t1 in FIG. 4, which is smaller, or steeper than the gradient $-V2/t2$. If the resultant gradient is smaller than the predetermined value then this indicates that the present change of SPL is made by SPR, in which case step 452 is executed. At the first processing of step 430, the CPU 3b decides SPL change of SPR does not occur, then processing proceeds around the loop of steps 440, 450, 410, 420, and 430, until the SPL change of SPR is detected in step 430. If SPR is detected in step 430, process proceeds to step 452. In step 452 SPR flag is set, then processing proceeds to step 410 through step 450. At the first, SPR is not detected in step 430, then processing proceeds to step 440.

In step 440, a decision is made as to whether convergence of an SPL change of SPR is detected. If convergence of the SPL change of SPR is detected, SPR convergence flag is set in step 440. At the first operation of step 440, the CPU 3b determines that SPR has been not converged, then processing returns to step 410 through step 450.

Figure 13B:
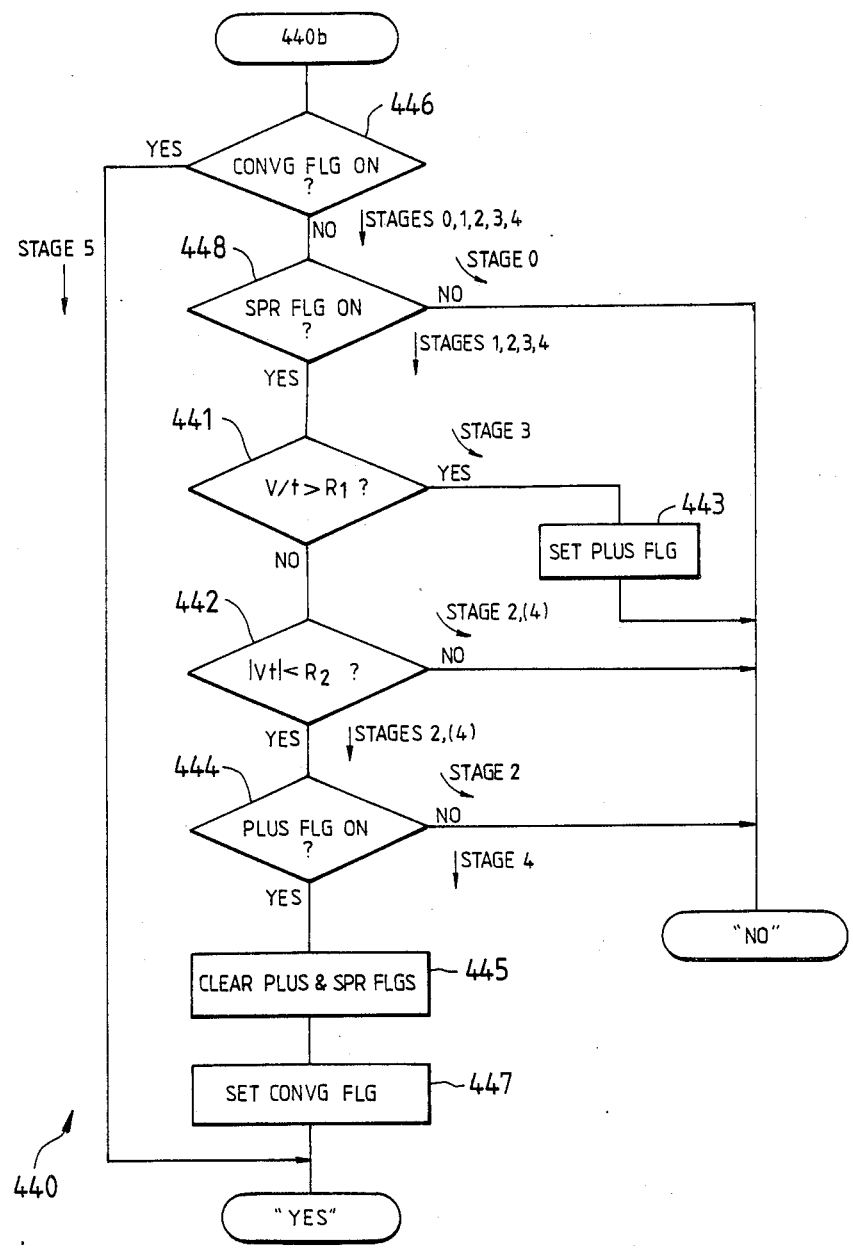

FIG. 13B shows the detailed steps of step 440 of FIG. 13A. The process of step 440 begins at step 440b. A determination is made in the following step 446, as to whether "convergence flag" has been set. If the "convergence flag" has been set, processing progresses to the outlet of the flow diagram, i.e., "YES" terminal. If the convergence flag is not set, a decision is made in the step 448, as to whether SPR flag has been set. If SPR flag has been set, the processing proceeds to step 441. A decision is made in step 441, as to whether gradient of SPL change is greater than a positive predetermined value R1. If a gradient is greater than the positive predetermined value R1, processing proceeds to step 443. At the first operation of step 441, a gradient is lower than the value R1 then this indicates that the SPL change enters negative slope change as shown by stage 1 in FIG. 8D. Then, a decision is made in step 442 as to whether a gradient of SPL is nearly equal to zero, then this indicates the present SPL to reach convergence of SPR pulse. At the first operation of step 442, the CPU 3b judges the gradient not equal nearly to zero then processing progresses to "NO" of step 440, i.e., to step 110. When SPL change enters the stage 3, the CPU 3b judges SPL change positive then setting a plus flag in step 441. In convergence stage of SPR, i.e., stage 4, processing proceeds through step 441, to step 442. The CPU 3b judges a gradient nearly equal to zero, and then the process progresses to step 444. A decision is made as to whether the plus flag has been set, then this indicates that SPL change has passed the bottom stage of SPL change of SPR. Therefore, if SPL change is at the bottom stage of SPR the operation progresses to "NO" of step 440. In convergence stage of SPR, processing progresses to step 445. Then, the CPU 3b detects convergence of SPL change of SPR. In the following step 445, the CPU 3b resets the plus and SPR flags. In the successive step 447, "convergence flag" is set. Then, processing proceeds to "YES" of step 440.

In FIG. 13A, processing progresses from the "YES" terminal to step 460. A combination of steps 460 and 470 provides a counter for processing cycle count. At first processing of steps 460 and 470, processing proceeds to step 480. In step 480, the CPU 3b stores values of SPL and calculates arithmetic mean as well as, calculating the set point SP from the resultant arithmetic mean, then processing progresses around the loop of steps 490, 410, 430, 440, 460, 470, and 480 until the loop count reaches 3 in counting steps 460 and 470 in order to confirm that SPR convergence status continues for a predetermined interval. However, if another SPR occurs during process of the loop of steps 490, 410, 430, 440, 460, 470, and 480, processing branches off at step 430 and proceeds to steps 450, then, the stored SPL data and convergence, plus, and flags are cleared and the CPU 3b begins storing new SPL data.

When the counting has finished, processing progresses to step 500. In step 500, CPU 3b compares a sampled SPL value with the set point value SP. If SPL is higher than the set point value SP, process return to step 410. If SPL is lower than the set point (stage 7), SPL change V/t is compared with a predetermined value S2 in step 510. In step 500, if the value of SPL gradient $-V/t$ is larger than the predetermined value S2, a drowsiness signal is outputted in step 520 (stage 8). If SPL gradient $-V/t$ is smaller than the predetermined value S2, i.e., SPL gradient is steeper than that determined by S2, this decrease of SPL can be determined as an SPL decrease of arousal level decrease because in step 430 this decrease was determined an SPL change other than that of SPR, i.e., of gradient range A. Then, the CPU 3b send the drowsiness signal to the buzzer 4 and air-condition controller 5 in step 520 in order to alarm and arouse the driver.

In this way, the arousal level judging apparatus judges a decrease in the arousal level of a driver by comparing SPL with the reference value which is obtained by sampling SPL just after SPR occurrence, as well as by detecting higher decrease ratio of SPL than a predetermined gradient ratio after SPL decreases to the set point which is obtained from the reference value. Therefore, the arousal level judging apparatus detects decrease in arousal level without effect of diurnal variation and of SPL decrease due to SPR. In addition, arousal level decrease can be detected without errors even if the predetermined value is set with a little margin. Therefore, arousal level decrement can be detected in the early stage of arousal level decrease.

In the first and third embodiment, a SPR convergence is detected by detection of stages 1, 3, and 4. However, several variation methods for detecting convergence of SPR variation can be considered. For example, in stage 4, if sampled SPLs does not change over a predetermined range for a predetermined time interval after detection of SPL change of stage 1, SPR convergence can also be detected. Moreover, SPL convergence can be detected by detecting SPL change entering stages 2 and 4, i.e., detecting twice ocurrences of zero gradient for after detection of SPR ocurrence. Further, there are various comparing means for arousal level detecting means. For example, one means is obtained by comparing the ratio of the present SPL value to the reference value with a predetermined value X. Another means is also obtained by comparing the difference between the present SPL value and the reference value with a predetermined value X. Therefore, there is provided arousal level detecting means for determing arousal state and non-arousal state of the human body using the relationship between the skin potential level and the reference value.

As described hereinabove, three embodiments of the arousal level judging apparatus according to the present invention detect arousal level decrease. However, this invention should not be limited to the above-mentioned embodiments. For example, this technique can be applied to doze alarm systems for various operations. Then, predetermined value T for detection of SPR and the predetermined value X of SPL decrease, and value S2 are changed in accordance with operations and circumstances.

Figure 10:
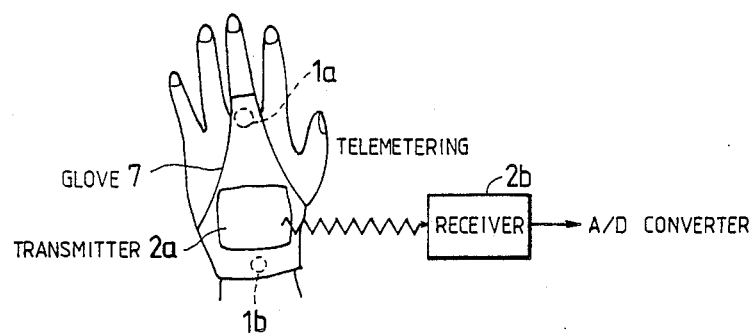
FIG. 10 is a block diagram of another preferred embodiment.

Moreover, detection electrodes 1a, 1b and detection circuit 2 may have variations. For example, as shown in FIG. 10, a driver puts on a glove 7 which has the detection electrodes 1a, 1b and a transmitter 2a transmitting detected SPL data which is received by a receiver 2b. Further, electrodes 1a, 1b may be provided to the steering wheel which is gripped normally when driving a car.

Further, in the first embodiment, the arousal level judging apparatus judges the driver at a low arousal level when SPL decrease ratio exceeds 60-80%. In the third embodiment, it is determined that SPL value of the set point S1 is 90% of the reference value, and the predetermined value S2 is compared with gradient of SPL V/t. These predetermined values may be changed in accordance with signals of detecting environmental changes within a car, such as room temperature of the car, sound level, or driving condition, and out-door environmental change, such as weather, day/night, or drive speed, traffic, presence of a passenger in order to provide surer arousal decrease detection.

In the above-mentioned embodiments, CPU 3b operates buzzer 4 and car air-conditioner 6. Stop signals may be made by a timer or detection of SPL increment or SPR occurrence.

The above-described embodiments are just examples of the present invention, and therefore, it will be apparent for those skilled in the art that many modifications and variations may be made without departing from the scope of the present invention.

What is claimed is:

1. An arousal level judging apparatus comprising:
   (a) skin potential level detection means for detecting a skin potential level of a human body;
   (b) level change detection means for detecting a degree of change in a level of an output signal of said skin potential level detection means over a predetermined interval;
   (c) a comparing means for comparing said degree from said level change detection means with a first predetermined value to detect a pulse-like change in said skin potential level;
   (d) convergence detection means responsive to an output signal from said comparing means for detecting a non-pulse like portion in said skin potential level by analyzing successive changes of gradient determined by said degree from said level change detection means;
   (e) storing means for storing said skin potential level as a reference value when said non-pulse like portion is detected by said convergence detection means; and
   (f) arousal level detecting means responsive to said skin potential level from said skin potential level detection means and to said reference value from said storing means for determining arousal state and non-arousal state of said human body using the relationship between said skin potential level and said reference value.

2. An arousal level judging apparatus as claimed in claim 1, wherein said convergence detection means comprises:
   a second comparing means for comparing said signal from said level change detection means with a second predetermined value which is of opposite sign to said first predetermined value; and
   a third comparing means responsive to said second comparing means for comparing said signal from said level change detection means with a third predetermined value.

3. An arousal level judging apparatus as claimed in claim 1, further comprising an alarm means responsive to said arousal level detection means for alarming.

4. An arousal level judging apparatus as claimed in claim 1, further comprising an input means for inputting a difference data of said skin potential level between high and low arousal state, said arousal level detection means responsive to said data and using said data to evaluate said relationship between said skin potential level and said reference value.

5. An arousal level judging apparatus as claimed in claim 4, further comprising an alarm means responsive to said arousal level detection means for alarming.

6. An arousal level judging apparatus comprising:
   (a) skin potential level detection means for detecting a skin potential level of a human body;

(b) level change detection means for detecting a degree of change in a level of an output signal of said skin potential level detection means over a predetermined interval;

(c) a comparing means for comparing said degree from said level change detection means with a first predetermined value to detect a pulse-like change in said skin potential level;

(d) convergence detection means responsive to an output signal from said comparing means for detecting a non-pulse like portion in said skin potential level by analyzing successive changes of gradient determined by said degree from said level change detection means;

(e) storing means for storing said skin potential level as a reference value when said non-pulse like portion is detected by said convergence detection means;

(f) a calculation means for obtaining a set point value by multiplying said reference value by a constant smaller than one; and (g) arousal level detection means for determining a non-arousal state of said human body when said skin potential level is below said set point value and the gradient of the change of said skin potential level below said set point value is greater than a second predetermined value.

7. An arousal level judging apparatus as claimed in claim 6, wherein said convergence detection means comprises:

a second comparing means for comparing said signal from said level change detection means with a third predetermined value which is of opposite sign to said first predetermined value; and a third comparing means responsive to said second comparing means for comparing said signal from said level change detection means with a fourth predetermined value.

8. An arousal level judging apparatus as claimed in claim 6, further comprising an alarm means responsive to said arousal level detection means for alarming.

9. A method of judging an arousal level comprising the steps of:

(a) detecting a skin potential level of a human body;

(b) detecting a skin potential response which is a pulse-like change in said skin potential level;

(c) determining a reference value as a skin potential level just after a convergence of said skin potential response, said convergence being a portion where said skin potential level reaches an end of said pulse-like change;

(d) calculating a decrease ratio of said skin potential level using said detected skin potential level and said reference value; and (e) comparing said decrease ratio with a predetermined value to judge an arousal level of said human body.

10. An arousal level judging apparatus comprising:

(a) detection means for detecting a skin potential level of a human body;

(b) means for detecting a skin potential response, which is a pulse-like change in said skin potential level;

(c) storing means for storing a reference value which is a skin potential level just after a convergence of said skin potential response, said convergence being a portion where said skin potential level reaches an end of said pulse-like change;

(d) means for calculating a decrease ratio of said skin potential level using said detected skin potential level and said reference value; and (e) comparing means for comparing said decrease ratio with a predetermined value to judge an arousal level of said human body.

11. An arousal level judging apparatus comprising:

(a) skin potential detection means having a pair of electrodes for detecting a skin potential level of a human body;

(b) computer means, responsive to said detection device, for: (a) detecting a pulse-like change of said skin potential level, (b) storing a reference value which is a skin potential level just after an end of said pulse-like change, and (c) detecting a decrease of an arousal level on the basis of a decrease of said skin potential level from said reference value and producing an alarm signal indicative thereof; and (c) alarm means, responsive to said alarm signal of said computer means for alarming when said decrease of an arousal level is detected by said computer means.

12. A method for detecting an end of a skin potential response of a skin potential level of a subject, comprising the steps of:

determining a gradient of said skin potential level;

setting an indication when said gradient is greater than a predetermined positive value; and subsequently determining, after said indication is set, that the gradient is equal to a value close to zero, and determining said end of said skin potential response based thereupon.

* * * * *